(12) United States Patent
Xie et al.

(10) Patent No.: US 9,058,520 B2
(45) Date of Patent: Jun. 16, 2015

(54) SYSTEMS AND METHODS FOR HANDS FREE INSPECTION

(75) Inventors: Binglong Xie, Lawrenceville, NJ (US); Yakup Genc, Dayton, NJ (US); Clifford Hatcher, Jr., Orlando, FL (US); Himanshu Bhatnagar, Charlotte, NC (US); Forrest R. Ruhge, Orlando, FL (US)

(73) Assignees: Siemens Corporation, Iselin, NJ (US); Siemens Energy, Inc., Orlando, FL (US)

( * ) Notice: Subject to any disclaimer, the term of this patent is extended or adjusted under 35 U.S.C. 154(b) by 453 days.

(21) Appl. No.: 13/617,801

(22) Filed: Sep. 14, 2012

(65) Prior Publication Data

US 2013/0083187 A1    Apr. 4, 2013

Related U.S. Application Data

(60) Provisional application No. 61/537,642, filed on Sep. 22, 2011.

(51) Int. Cl.
| | |
|---|---|
| *G01C 19/06* | (2006.01) |
| *G06K 9/00* | (2006.01) |
| *G01N 21/95* | (2006.01) |
| *G01N 21/954* | (2006.01) |
| *G06Q 10/00* | (2012.01) |
| *G06Q 50/06* | (2012.01) |

(52) U.S. Cl.
CPC ........ *G06K 9/00624* (2013.01); *G01N 21/9515* (2013.01); *G01N 21/954* (2013.01); *G06Q 10/20* (2013.01); *G06Q 50/06* (2013.01)

(58) Field of Classification Search
CPC .......... H04N 21/47815; H04N 21/643; H04N 7/185; H04N 21/8586; H04N 21/47202; G01N 21/87
USPC ............................................ 348/143, 125, 92
See application file for complete search history.

(56) References Cited

U.S. PATENT DOCUMENTS

| | | | |
|---|---|---|---|
| 4,742,227 A | 5/1988 | Takenaka | |
| 4,811,091 A | 3/1989 | Morrison et al. | |
| 6,487,922 B1 | 12/2002 | Bauer et al. | |
| 7,075,296 B2 | 7/2006 | Moore | |
| 7,756,679 B2 | 7/2010 | Nagafuchi et al. | |
| 2003/0093797 A1* | 5/2003 | Bazzaz | 725/74 |
| 2005/0091311 A1* | 4/2005 | Lund et al. | 709/203 |

(Continued)

OTHER PUBLICATIONS

PCT International Search Report mailed Dec. 21, 2012 corresponding to PCT International Application No. PCT/US2012/055871 filed Sep. 18, 2012 (11 pages).

*Primary Examiner* — Sath V Perungavoor
*Assistant Examiner* — Clifford Hilaire

(57) ABSTRACT

Systems and methods for inspecting a device are disclosed. The method includes arranging the device in a known position relative to a plurality of movable cameras. The plurality of movable cameras is mounted on a controllable actuator. The plurality of cameras is pointed at the device by controlling the controllable actuator to position the camera with a user interface. An image of the device generated by the camera is displayed on a mobile and wireless display. The computing device also causes a rendered virtual image of the device to be displayed on the mobile and wireless display. A stream of interest and a region of interest is selected at the mobile and wireless display from the images generated by the cameras.

19 Claims, 9 Drawing Sheets

(56) References Cited

U.S. PATENT DOCUMENTS

| | | | |
|---|---|---|---|
| 2006/0097719 A1* | 5/2006 | Moore | 324/237 |
| 2007/0002133 A1 | 1/2007 | Metala et al. | |
| 2007/0217672 A1 | 9/2007 | Shannon et al. | |
| 2008/0247635 A1 | 10/2008 | Davis et al. | |
| 2009/0154293 A1 | 6/2009 | Sengupta et al. | |
| 2009/0228133 A1 | 9/2009 | Loda | |
| 2010/0132137 A1* | 6/2010 | Eggleston | 15/21.1 |
| 2011/0128370 A1* | 6/2011 | Booth et al. | 348/125 |

\* cited by examiner

SYSTEMS AND METHODS FOR HANDS FREE INSPECTION

STATEMENT OF RELATED CASES

The present application claims priority to and the benefit of U.S. Provisional Patent Application Ser. No. 61/537,642 filed on Sep. 22, 2011, which is fully incorporated herein by reference.

TECHNICAL FIELD

The present invention relates to inspection systems and methods that use cameras and computing devices. More particularly, it relates to systems and methods for inspecting turbines.

BACKGROUND

For industrial devices and equipment, computerized inspection from camera images provides very accurate information. However, if the object being inspected is complex (for example, a modern gas turbine machine), and when multiple cameras and multiple configurations of cameras are involved, inspection becomes difficult. Data related to a device that is inspected is often stored in a database. Sometimes, multiple cameras record images of different parts of the device which have to be processed by a processor before being applied to the inspection. An inspector often moves around a large object, such as a turbine that is inspected.

It is often difficult for the inspector to rapidly access, during a walk-around, a powerful computer with data related to the object, especially in an industrial environment of a turbine. This hampers the productivity of inspection.

Another reason for this difficulty is because the devices are large and have complex shapes which can be difficult to analyze without computer support. These machines also have inter-related parts and components that mutually influence each other. For instance, actuating a valve may affect turbine rotator speed, temperature and vibrations, which all may require inspection of different parts at different locations of the machine. Inspection data may be aggregated at a powerful computer. However, it is not efficient for an inspector to have to move between the object and a computer to conduct an inspection.

Accordingly, new and improved systems and methodologies computer assisted hands-free inspection of complex devices are needed.

SUMMARY

The present invention provides direct support to let an inspector inspecting a device be aware of the exact situation of the camera configuration with respect of the device being inspected. In accordance with one aspect of the present invention, cameras are installed on an actuator which can be controlled from the computer with user interface devices including joysticks, keyboard and mouse. The cameras can have multiple degrees of freedom. Software in a computing device fully controls the actuators and knows the spatial location and orientation of each camera. Camera images are transmitted from a computer wirelessly to a mobile and wireless computer device with a display to display images. A user can select from the mobile computer device a stream of interest from multiple image streams to be sent from the computer to the mobile computing device. A user can also select a region of interest in a selected stream of interest to be transmitted from the computer to the mobile computing device. The image data outside the selected region of interest in a selected stream of interest is not transmitted from the computer to the mobile computing device.

In accordance with an aspect of the present invention a method is provided for inspecting a turbine with an inspection computer and a camera, comprising with a wireless mobile device, establishing wireless connectivity with the inspection computer, selecting a stream of interest of images of the turbine and a region of interest within the stream of interest with the wireless mobile device, the wireless mobile device requesting the stream of interest and the region of interest from the inspection computer and then receiving images representing the region of interest in the stream of interest from the inspection computer and the wireless mobile device displaying the region of interest.

In accordance with a further aspect of the present invention a method is provided, wherein a list of a plurality of streams of interest is displayed on the mobile wireless device and the stream of interest is selected from the list and the region of interest received from the inspection computer is retrieved from a memory connected to the inspection computer.

In accordance with yet a further aspect of the present invention a method is provided, wherein a list of a plurality of streams of interest is displayed on the mobile wireless device and the stream of interest is selected from the list and the region of interest received from the inspection computer is retrieved from the camera connected to the inspection computer.

In accordance with yet a further aspect of the present invention a method is provided, wherein the wireless mobile device selects a frame per second parameter for the image stream of interest and the inspection computer sends the image stream of interest to the wireless mobile device in accordance with the selected frame per second.

In accordance with yet a further aspect of the present invention a method is provided, wherein the selected frame per second is less than 30 frames per second.

In accordance with yet a further aspect of the present invention a method is provided, comprising the wireless mobile device sending probe control signals to the inspection computer and the inspection computer processing the probe control signals to send processed probe control signals to control a probe.

In accordance with yet a further aspect of the present invention a method is provided, comprising the wireless mobile device sending camera control signals to the inspection computer and the inspection computer processing the camera control signals to send processed camera control signals to control the camera.

In accordance with yet a further aspect of the present invention a method is provided, comprising the wireless mobile device sending trigger control signals to the inspection computer and the inspection computer processing the trigger control signals to send processed trigger control signals to control a trigger board.

In accordance with yet a further aspect of the present invention a method is provided, comprising the wireless mobile device sending probe control signals to the inspection computer and the inspection computer processing the probe control signals to send processed probe control signals to control a probe, sending camera control signals to the inspection computer and the inspection computer processing the camera control signals to send processed camera control signals to control the camera, and sending trigger control signals to the inspection computer and the inspection computer processing the trigger control signals to send processed trigger control signals to control a trigger board.

In accordance with yet a further aspect of the present invention a method is provided, comprising the wireless mobile device sending a request to the inspection computer for a model of the turbine in a region of interest and for an image of the turbine in the region of interest, receiving the model of the turbine and the image of the turbine in the region of interest from the inspection computer and displaying the model of the turbine and the image of the turbine in the region of interest on the wireless mobile device.

In accordance with yet a further aspect of the present invention a method is provided, further comprising the inspection computer transmitting the region of interest within the stream of interest of images at a frame rate that depends on a transmission quality with the wireless mobile device.

In accordance with another aspect of the present invention a system is provided to inspect a turbine with an inspection computer and a camera, comprising: a wireless mobile device, enabled to establish wireless connectivity with the inspection computer, wherein the wireless mobile device includes a processor enabled to execute instructions to perform the steps: selecting a stream of interest of images of the turbine and a region of interest within the stream of interest, requesting the stream of interest and the region of interest from the inspection computer and then receiving images representing the region of interest in the stream of interest from the inspection computer and displaying the region of interest on a display.

In accordance with yet another aspect of the present invention a system is provided, wherein a list of a plurality of streams of interest is displayed on the mobile wireless device and the stream of interest is selected from the list and the region of interest received from the inspection computer is retrieved from a memory connected to the inspection computer.

In accordance with yet another aspect of the present invention a system is provided, wherein a list of a plurality of streams of interest is displayed on the mobile wireless device and the stream of interest is selected from the list and the region of interest received from the inspection computer is retrieved from the camera connected to the inspection computer.

In accordance with yet another aspect of the present invention a system is provided, wherein the wireless mobile device selects a frame per second parameter for the image stream of interest and the inspection computer sends the image stream of interest to the wireless mobile device in accordance with the selected frame per second.

In accordance with yet another aspect of the present invention a system is provided, wherein the selected frame per second is less than 30 frames per second.

In accordance with yet another aspect of the present invention a system is provided, comprising the wireless mobile device sending probe control signals to the inspection computer and the inspection computer processing the probe control signals to send processed probe control signals to control a probe.

In accordance with yet another aspect of the present invention a system is provided, comprising the wireless mobile device sending camera control signals to the inspection computer and the inspection computer processing the camera control signals to send processed camera control signals to control the camera.

In accordance with yet another aspect of the present invention a system is provided, comprising the wireless mobile device sending trigger control signals to the inspection computer and the inspection computer processing the trigger control signals to send processed trigger control signals to control a trigger board.

In accordance with yet another aspect of the present invention a system is provided, further comprising: the inspection computer transmitting the region of interest within the stream of interest of images at a frame rate that depends on a transmission quality with the wireless mobile device.

Systems to perform the above described methods and other methods described herein are also provided in accordance with aspects of the present invention.

A computing device is connected to each controllable actuator and to the at least one display and includes a user interface to control each controllable actuator. The computing device also causes the rendered virtual image to be displayed on the at least one display.

DRAWINGS

DESCRIPTION

It is often difficult for an inspector of complicated machinery to obtain a full and unobstructed view of certain parts of the machinery. Many times it is desirable to view multiple parts of the machine at the same time. It is well known that a change or modification at a machine or an environment of a machine part can affect the machine elsewhere at a part that is not directly visible to an inspector at one location.

It is also desirable in some situations to place a visual current condition of a machine during an inspection in a context of a previous condition that was recorded during an earlier inspection.

In a separate and co-pending patent application co-owned by the same assignee a side-by-side inspection system was described to give situational awareness in a complex visual inspection. In such as system with a side-by-side approach the user works in front of a PC (desktop or laptop), to which all the cameras and a probe controller are connected. A probe in one embodiment of the present invention is attached to a navigable device such as a robotic arm which is controlled by a probe controller. The probe itself may be a camera, a temperature sensor, or any other sensor or actuator that can be attached to the navigable device. A plurality of probes, for instance a camera and a temperature sensor may be attached to the navigable device. Movement of the navigable device or navigation is controlled by an operator via a probe controller.

Because the actual device being inspected, for example, a gas turbine machine, is often very large, the user has a need to walk around the machine and check the actual situation while performing inspection. It would be beneficial to free the user from sitting in front that PC or having to return to the PC, and allow him or her to check the actual device, while still having access to the inspection control PC. In accordance with an aspect of the present invention methods and systems for inspection and data collection are provided that allow the user to use a light-weight mobile computer tablet instead of working at a bulky desktop or laptop PC for most of the inspection work.

Figure 1:
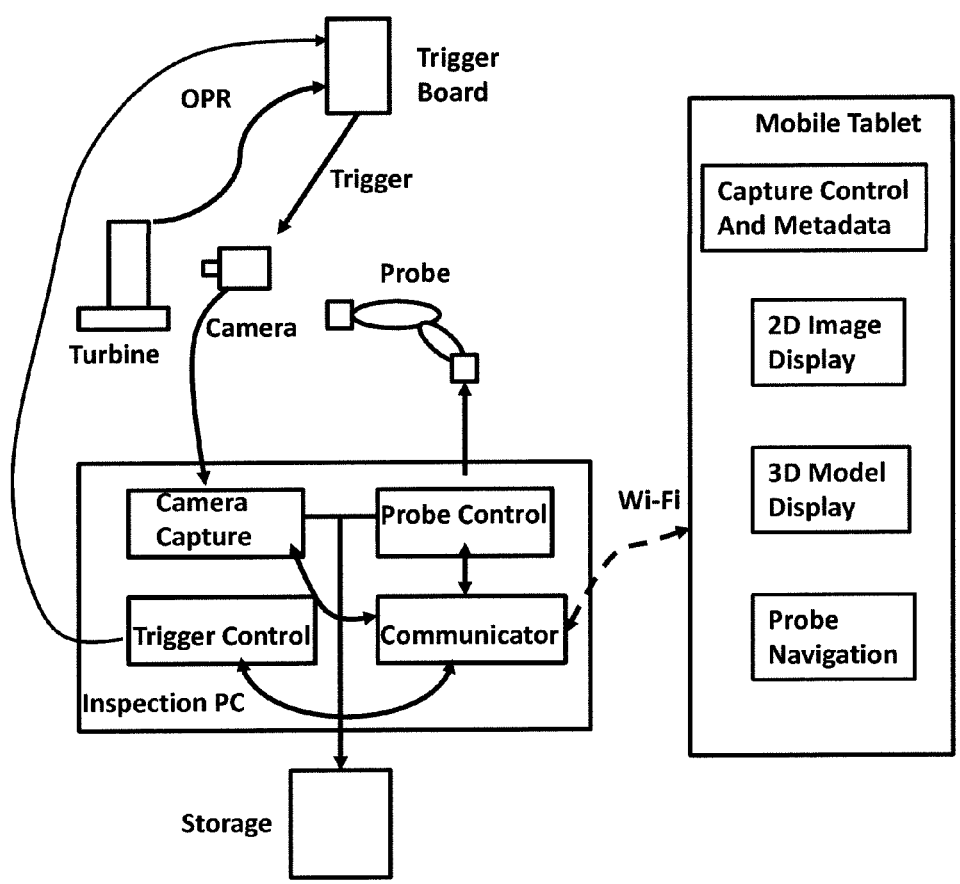
FIG. 1 illustrates a system for inspecting a device in accordance with an aspect of the present invention.

FIG. 1 illustrates one embodiment of the present invention. The system in FIG. 1 includes an Inspection PC, which is a desk top or a lap top computer, for instance. The Inspection PC has a Communicator module that handles the communication with the Mobile Tablet, which is for example an iPad®. A tablet includes a processor, a wireless communication device to communicate with an exterior device, a display and a data input device, which may be a touchscreen over the display. Preferably, the tablet includes a camera.

The communication link between the Inspection PC and the Mobile Tablet is wireless, for example, through Wi-Fi. The Inspection PC includes a Camera Capture to capture data generated by the camera. Either in the Inspection PC or on a separate Trigger Board a processor is enabled to generate a trigger signal that instructs a camera to record or a processor to select an image from a series of images recorded by the camera. The processor on the Trigger Board receives an OPR signal from a Once Per Rotation (OPR) sensor in a turbine to alert when a reference turbine blade passes the sensor. From the OPR signal a trigger moment for the camera is generated and the camera takes an image of a Turbine blade at the calculated moment.

The specific image is captured and may be stored on a data Storage device such as a magnetic disk. The Inspection PC contains a Trigger Control which receives input, preferably through a Graphics User Interface (GUI) from a user to set the desired trigger moment and required offsets.

The Communicator in one embodiment of the present invention streams the live videos from cameras to the Mobile Tablet. It accepts requests of capture control, meta data change, and probe navigation from the Mobile Tablet, and commands the camera capture, trigger control and probe control to carry out the action.

Figure 2:
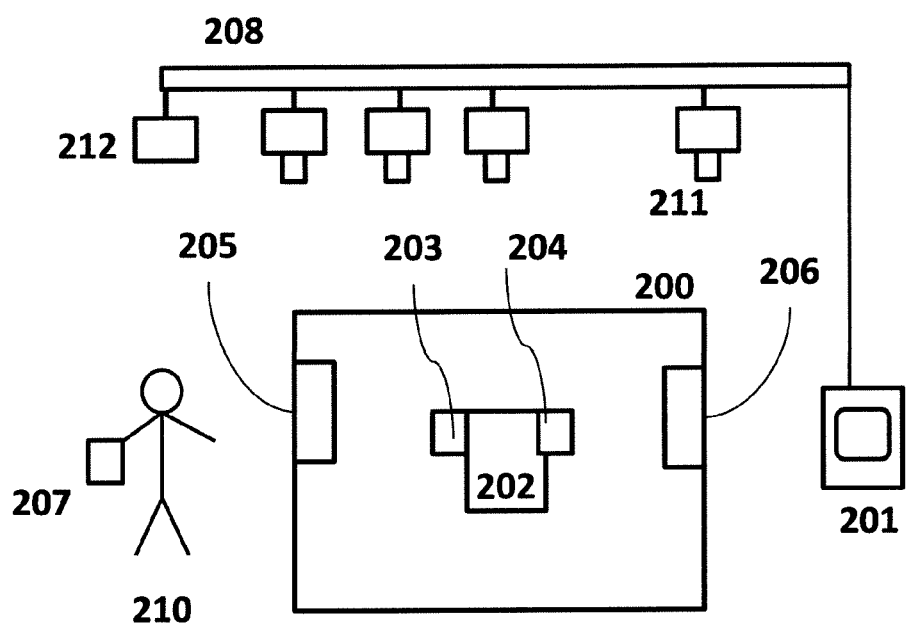
FIG. 2 illustrates the use of a mobile tablet in accordance with an aspect of the present invention.

FIG. 2 illustrates one scenario in which a mobile tablet is useful for inspection. A large machine 200 has a part 205 that needs visual inspection by an inspector 210 with a mobile tablet 207. The machine 200 has a driving part 202 that is monitored by one or more probes 203, which may include a camera and is controlled by a controlling device 204 which may include an actuator. The controlling device 204, which may be a valve, can be opened and closed from a computer 201. The computer 201 is connected to a network 208 to which a series of sensors, such as camera 211 which monitors 206, are connected which can be monitored by computer 201. Another part 206 on machine 200 and part 205 are both affected by a condition of 202. An inspector 210 with a tablet computer on a location near device 205 is away from computer 201 and cannot see 206. In a harsh EM environment the network 208 includes preferably a shielded cable or an optical cable.

Under certain conditions, it is preferable that the inspector directly views device 205 to see in real-time and from his best perspective what is happening with device 205 when 202 is changed in performance. The inspector also would like to see what is happening at device 205 as a consequence of a setting or performance of 202. The device 202 is controlled from 201. One known approach is to involve multiple inspectors, one at 201, one at 206 and one at 205 all provided with telephones or radio devices to coordinate activities and observations. This is not an ideal solution, as the level of coordination required leaves sufficient room for error and misinterpretation. Furthermore, the harsh environment is not conducive to the use of radio or audio communications. Also, some events may require a quick reaction which may not be facilitated by the working conditions around machinery and by involving two or more individuals.

The device 200 is one embodiment of the present invention is monitored by cameras, such as camera 211, which are connected to a network 208. In order to facilitate wireless communication a router or hub 212 such as a Bluetooth hub for wireless communications may be attached to the network 208. Special cameras may also be attached to the object. For instance an Infra-Red (IR) camera may be attached to a port of a turbine to monitor hot parts of the turbine. The IR camera images are also available on computer 201.

Clearly, it would be beneficial for an inspector to view relevant data of a component while viewing its operation. For instance, in one embodiment an inspector observes a part, its image and background information, such as a CAD model of the part. This allows the inspector to view the part in its context, and with the image data and the CAD data, detect any significant differences in its shape, for instance. An inspector with the help of the tablet device 207 also view a part of the object that is related to the location where he or she is standing but that is not visible from that position, by using the images that are available on 201 from cameras, or any other related data.

The use of a tablet, or an even smaller smart phone 207 in wireless contact with a computer 201 has several limitations that need to be addressed. (1) it has a display screen that is much smaller than the display of computer 201, which may have multiple screens; (2) wireless communications from device 207 to 210, even via a hub 212 may be restricted by its bandwidth; (3) processing and/or storage capability at 207 may be limited, providing a limited capacity of handling very large data streams for processing and display.

Figure 3:
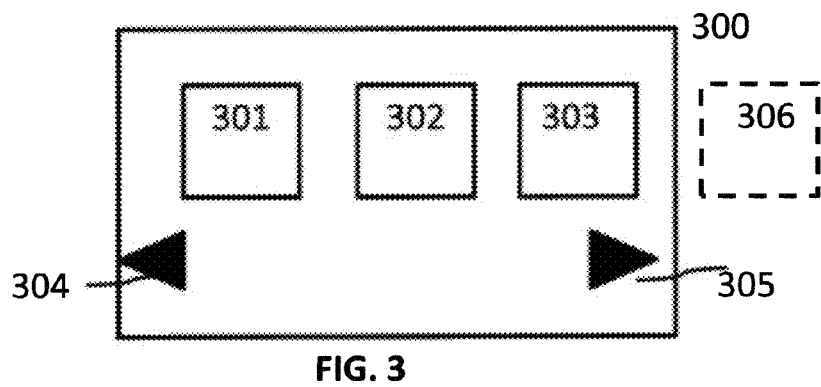
FIG. 3 illustrates the use of a mobile tablet in accordance with an aspect of the present invention.

At least for the above reasons and in accordance with an aspect of the present invention an inspector is enabled to select on device 207 one or more streams of images of interest (SOI) and within a stream a region of interest (ROI). This is illustrated in FIG. 3. It illustrates in diagram a display of device 207 with images 301, 302 and 303. The images 301, 302 and 303 are in one embodiment of the present invention static images or photographs each displayed in a window as is known in the art and obtained from three different cameras. In one embodiment of the present invention, at least one image is a video image. In one embodiment of the present invention at least one image is a video image at a slower display rate than the rate at which it was recorded by the camera. In one embodiment of the present invention menu items 304 and 305 are displayed on the display.

In one embodiment of the present invention display 300 has a touch screen whereon menus and menu items can be activated of de-activated, windows can be sized or resized and items and windows on a screen can be selected, moved, activated and subjected to any action which are known and available on touch screen based computers. By activating item 304 or 305 on a touch screen, for instance with a touch pen, the images 301, 302 and 303 will be moved to the left or the right respectively, and will disappear from the screen as they reach and pass the edge of the screen and additional images will appear on the opposite side of the screen. This is illustrated with an image 306 that is outside the space of the display in a virtual space. When menu item 304 is activated all the images move to the left. Eventually image 301 will disappear from the screen on the left and image 306 will appear on the right side of the screen.

Figure 4:
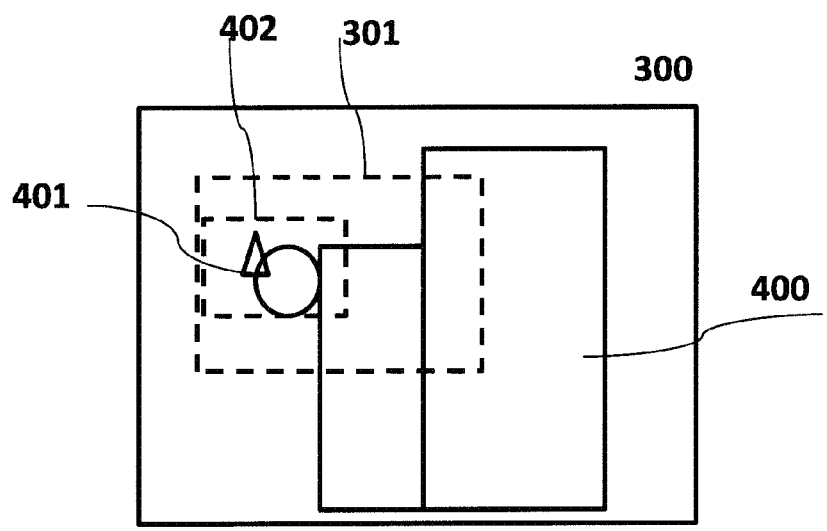
FIG. 4 illustrates a display on a mobile tablet used for turbine inspection in accordance with an aspect of the present invention.

This allows a small screen 300 to display a range of images of cameras to be selected for display during inspection. By selecting an image, for instance by touching it with a touchpen on the screen, the image in enlarged and displayed on a larger part of the screen 300. FIG. 4 illustrates an activated and enlarged image 301 on screen 300 which shows an image of a device 400 with a part 401 which is of interest for viewing. In one embodiment of the present invention the image 301 is shown with an image of device 401. A user draws or activates a window 402 around 401 to initiate and set the region of interest. In one embodiment of the present invention the system 201 applies knowledge of the location of the camera relative to the device and CAD data of the device to generate a drawing of the device 400 to identify the location of 401 in device 400. In general, such a context image needs not to be drawn on a small screen for viewing 401. However, when several cameras are being used, it may be helpful to an inspector to recall the context of the window 401. By activating a menu the image on a screen 300 may be resized to temporarily show the window 402 in the context of the CAD drawing of device 400. One can see that the maximum image of the camera generated image is 301 which is smaller than the overall size of the CAD drawing.

In one embodiment of the present invention a brief description or label which may include an orientation and relative location is attached to a window with an image. The label can be displayed on demand.

Figure 5:
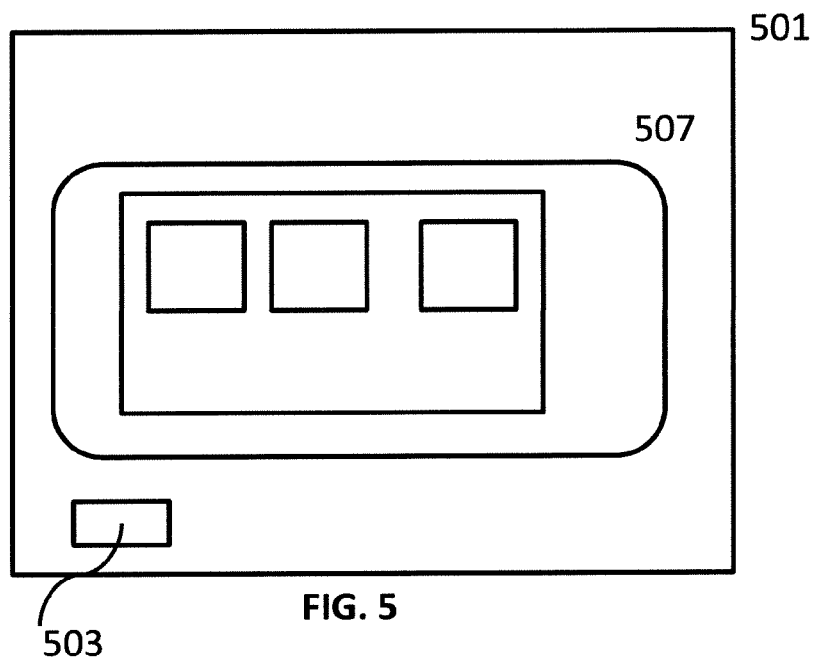
FIG. 5 illustrates a set up of a mobile inspection tablet in accordance with an aspect of the present invention.

Selection and preparation of ROIs and SOIs can take place on device 207 and/or on device 201. Because computer 201 is much more powerful and has a bigger display than 207 it may be beneficial to do an inspection preparation on computer 201 to set all preferences and synchronize the setting of device 207 with the inspection settings of device 207. During synchronization of devices 207 and 201, the device 201 is informed of the properties of device 207, including screen size. The set-up for device 207 can be performed on computer 201 or a similar powerful computer. This is illustrated in FIG. 5. It illustrates a display 501 of a powerful computer such as 201 with access to all the relevant cameras, sensors, databases and other devices and actuators that are relevant to an inspection. It shows an image 507 of device 207 that has to be configured. One can develop the desired configuration of 207 on display 501 with computer 201. Customizable data can be entered via a window 503. This may include a characterization of the transmission conditions between the device 207 and computer 207 and will affect frame rate, resolution, number of streams and the like.

A camera may have a relative wide field of vision and apply high resolution image sensors compared to the area of interest. Use of an image processor allows a limited number of image frames to be selected out of a stream of video images and a smaller area of interest to be captured, transmitted and displayed. This was illustrated in FIG. 4 which shows in diagram an image 301 of a large object with a smaller object of interest 401 that can be viewed in a window 402 by enlarging the image to a size of a screen 300 without significant loss of detail.

Assume that the object 401 is located in a high EM interference environment. The image 301 is recorded by a camera. In one embodiment of the present invention one would like to transmit image from the camera to a portable and mobile computing device 207 via a wireless channel. An inspector operating close to the object would thus be able to view a detailed image of 401. However, in that scenario computing device 201 in FIG. 2 has to transmit the entire image for processing over to 207. Due to for instance radio interference in a harsh environment device 207 may not be able to receive the video images as generated by the camera and provided by 201. It may also be the case that device 207 is not able to process and/or display the images as provided by 201. In that case it may be advantageous to instruct 201 to process images and send a down-sized version of the camera generated images to mobile device 207. Downsized herein may be, smaller in image area, a lower frame rate (down to a single image) and lower resolution.

It is known that one can exchange noise and/or bandwidth against time to transmit information error-free over a channel with noise and/or a limited bandwidth. In one embodiment of the present invention a high noise limited bandwidth wireless channel to device 207 is assumed that provides a capacity of only up to 10 kbit/sec for transmission of data. In accordance with an aspect of the present invention, computer device 201 is configured to transmit an image configured to meet the requirement of 10 kbit/sec to device 207 for display.

In accordance with an aspect of the present invention, one can provide an adaptive data transmission system between 201 and 207 over a wireless channel, based on exchange of known data sequences for instance. The devices 201 and 207 will set transmission and reception methods, including transmission rate and error correcting coding methods, based on the quality of the channel. In one embodiment of the present invention the devices 201 and 207 may be programmed based on a worst case scenario, wherein the channel is assumed to sustain a predefined transmission rate, but not more. Such an assumed transmission rate in one embodiment of the present invention is not greater than 10 kbit/sec. Such an assumed transmission rate in one embodiment of the present invention is not greater than 100 kbit/sec. Such an assumed transmission rate in one embodiment of the present invention is not greater than 1 Mbit/sec. Such an assumed transmission rate in one embodiment of the present invention is not greater than 10 Mbit/sec. Such an assumed transmission rate in one embodiment of the present invention is greater than 10 Mbit/sec.

In case the bandwidth is sufficient for real-time transmission and reception of multiple streams of video data, settings of device 207 are in general determined by the capacity and ability of device 207 to display images and not by the bandwidth.

In one embodiment of the present invention a GUI 600 is opened on a computer screen to display an image generated by a camera. It shows an image 301 generated by a camera. A window 402 is selected by an operator to display a region of interest on mobile device 207. One can set further preferences in the GUI, such as a time period for recording, a preferred frame rate, a display in real-time or slowed down, if one wants to provide a context (still) background image wherein window 402 has current image, set the timing of images when recorded at a lower frame rate, the size of the window, a resolution, black/white display and the like.

Figure 6:
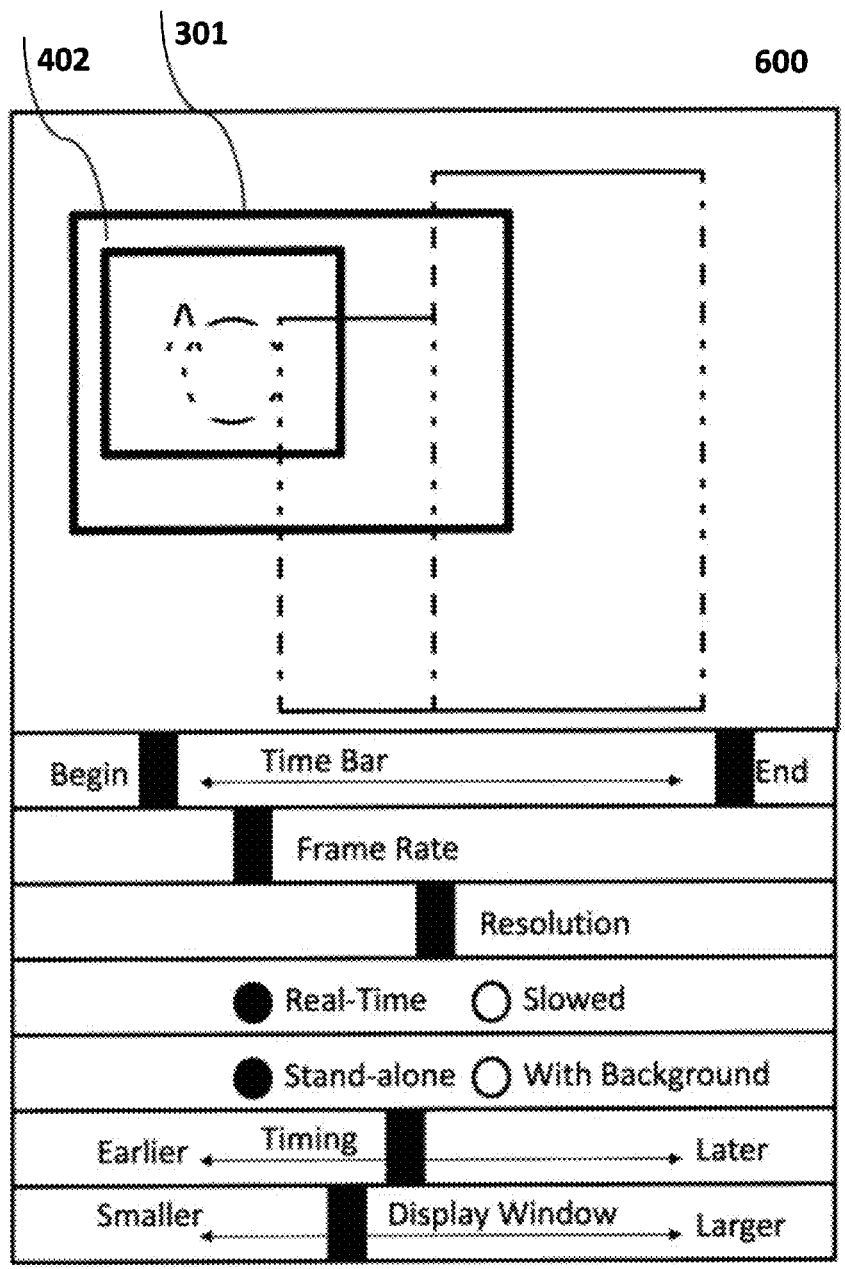
FIG. 6 illustrates a GUI used on the mobile inspection tablet in accordance with an aspect of the present invention.

The menu items of FIG. 6 may be independent in setting when bandwidth is sufficient and all settings are based on operator convenience. However, when bandwidth is limited the different setting may be connected, so that for instance a higher resolution is achieved at a cost of frame rate. All data is available in the powerful machine 201 and it is in general a bandwidth or processing limitation that will restrict the transfer of data to the mobile device.

Figure 7:
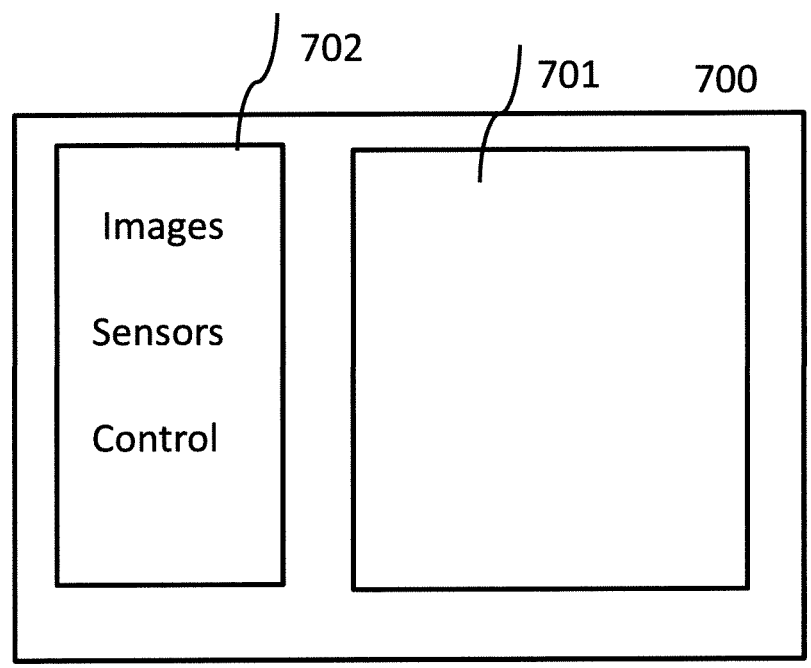
FIG. 7 illustrates a display on a touch screen of the mobile inspection tablet in accordance with an aspect of the present invention.

In one embodiment of the present invention the mobile device 207 has a GUI that can be activated on a touch screen 700 as illustrated in FIG. 7. An image is displayed on the screen 700 of a mobile device that applies all or most of the screen to display a region of interest (ROI) of one stream of interest (SOI). In one embodiment of the present invention a menu 702 is activated with at least three menu items: Images, Sensors and Control. The displayed image is reduced to a size 701. In one embodiment 701 is so small that no details can be viewed but only exist as a reminder for the viewing window which can be activated by touching it with the touchpen. The Images item allows to call up a new ROI or a new SOI with a particular ROI; the Sensors item allows to call up and view sensor data; and the Control item allows to select a machine setting which is transferred from mobile computer 207 to the computer 201 to instruct the machine.

In one embodiment of the present invention a camera, a machine connected to a central computer and a mobile computer which is enabled to receive a video stream of interest or a region of interest from the central computer are all located in a single room which is not bigger than 100 square meter. In one embodiment of the present invention at least one of the camera, the central computer and the mobile computer are not in a single room.

It has been discussed above that the mobile computer 207, which is a tablet computer or a smart phone and may be called a Mobile Tablet runs specialized software to present a GUI to the user. The user can select one or more camera videos, as well as a 3D view for instance of a related CAD model as main display with the data from the computer 201 which may be called an Inspection PC. It also features the capture control, metadata display, and probe navigation to allow the user to perform respective actions.

In such a configuration, after the initial hardware and software is setup, the user carries the tablet, and is free to walk around the subject of inspection without losing capabilities of performing inspection.

As discussed, the industrial field environment is often not electromagnetic friendly to get most out of Wi-Fi bandwidth due to strong electromagnetic interference, while the video streaming or 3D view streaming needs a significant bandwidth or data throughput capabilities. In accordance with an aspect of the present invention streams of interest (SOI), and regions of interest (ROI) are defined, preferably from the Mobile Tablet. Among the various camera videos and the 3D view, the user can choose one or more streams (SOIs) for viewing. Other streams will not be transferred to save the bandwidth. With each SOI, depending on the tablet screen estate availability, it allows the Mobile Tablet to choose a region of interest (ROI) to be transferred, and does not transfer the portion of the image that is not visible or not desired on the Mobile Tablet. Transferring only SOIs/ROIs requires less bandwidth than transferring all available images and improves the user experience.

Figure 8:
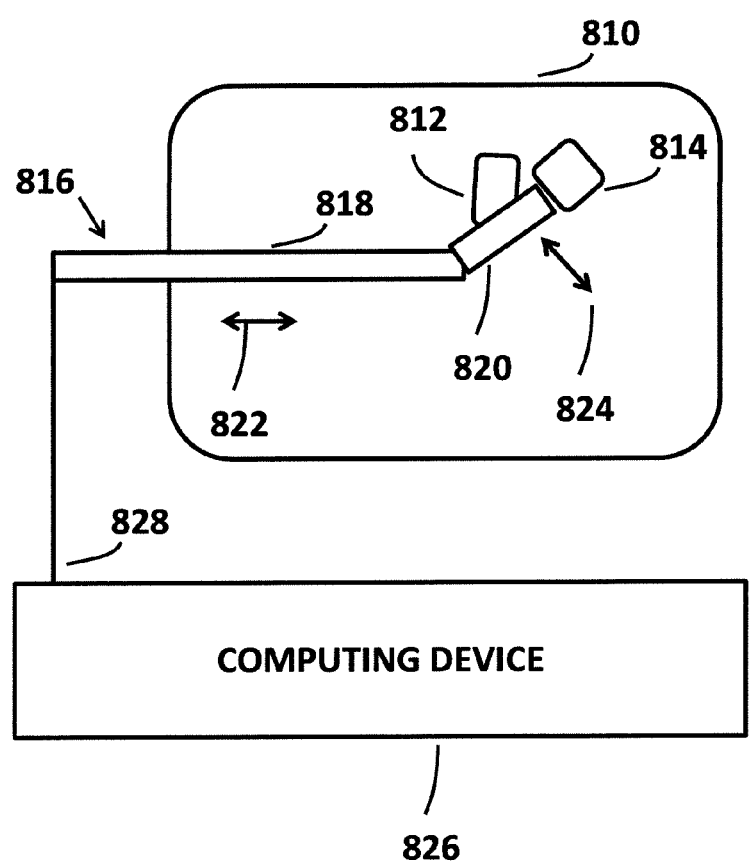
FIG. 8 illustrates the inspection of a turbine using the mobile inspection tablet in accordance with an aspect of the present invention.

FIG. 8 further illustrates a device being inspected and an inspection system in accordance with an aspect of the present invention. A device 810 being inspected is illustrated. The device 810 can be any of a large number of devices, including turbines, gas turbines and the like. The devices being inspected can be quite complex, both in size and in shape. When using a camera to do the inspection, it is quite easy to lose track of where a defect is located. The defects can include scars, cracks, stains and other defects. One may also inspect a performance of a device that has no visible defect.

A plurality of cameras 812 and 814 is moved inside the device 810 being inspected to conduct the inspection. The cameras 812 and 814 are mounted on a movable, controllable actuator 816. In accordance with an aspect of the present invention, the actuator 816 includes a first arm 818 and a second arm 820.

Although two cameras 812 and 814 are illustrated, a single camera can be used. Alternatively, more than two cameras can also be used.

The first arm 818 can be controllable moved along the direction indicated by arrow 822. Thus, the cameras 812 and 814 can be moved through the center of the device 810 being inspected to perform the inspection.

The second arm 820 can be rotated in the direction indicated by arrow 824. The second arm 820 can also be rotated in and out of the figure. Thus, the controllable movable actuator 816 has multiple degrees of freedom. As the actuator 816 is moved along direction 822, the second arm 820 can be rotated to examine all internal sections of the device 810 being inspected.

In accordance with another aspect of the present invention, a transmission circuit is attached to the actuator 816 to communicate the actuator 816 position and orientation to a computing device 826 via the interface 828. The transmission circuit can also transmit all of the physical characteristics of the cameras 812 and 814 to the computing device 826. In this way, the computing device 826 knows what the cameras 812 and 814 are looking at on the device 810 and the computing device 826 understands the characteristics of the cameras 812 and 814.

Figure 9:
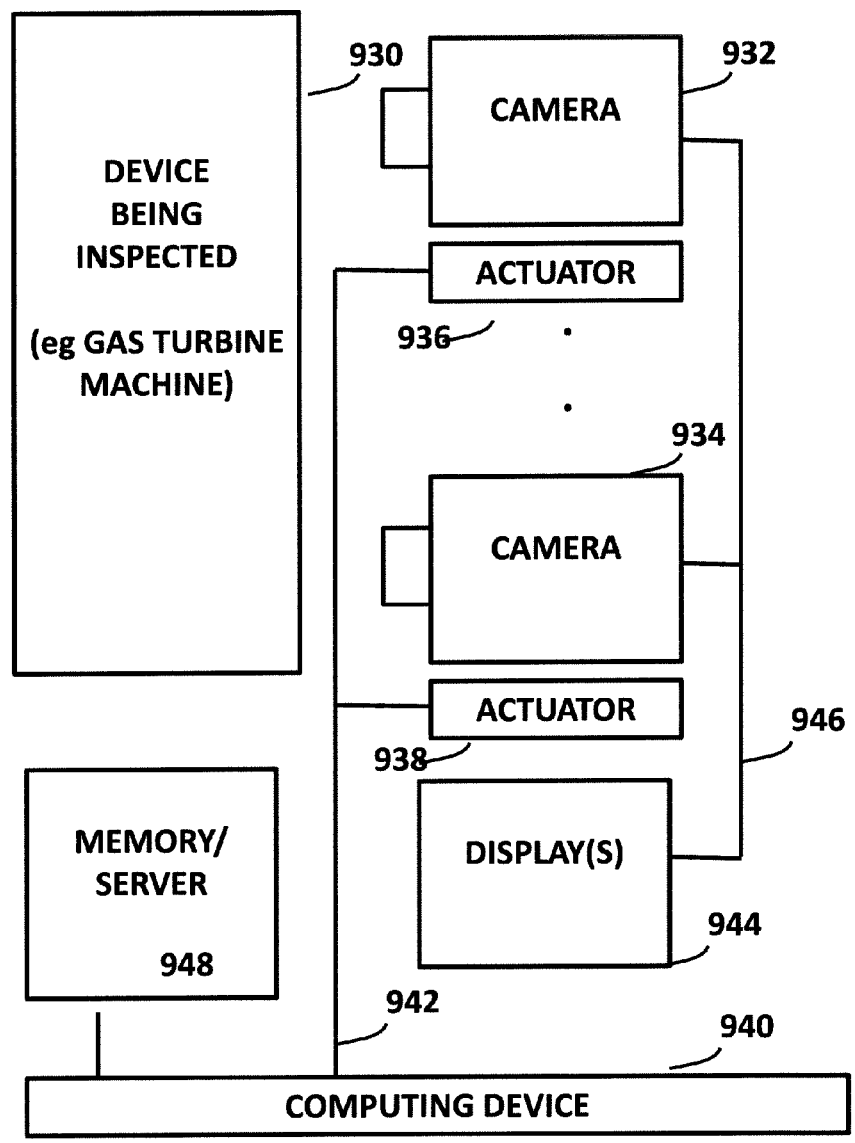
FIG. 9 illustrates a system for inspecting devices in accordance with an aspect of the present invention.

The system for inspecting devices in accordance with an aspect of the present invention is further illustrated in FIG. 9. A device 930 that is to be inspected is illustrated. The device is typically a complex device, such as a gas turbine machine.

The system includes a plurality of cameras 932 and 934. As before, although two cameras are shown, more than two cameras can be utilized. In accordance with other aspects of the present invention, a single camera can be used. The types of cameras used are standard industry cameras used to perform inspection of complex device.

Each of the cameras 932 and 934 are attached to an actuator 936 and 938, respectively. In accordance with an aspect of the invention, the actuators 936 and 938 are part of a single structure that includes multiple parts. Alternatively, each actuator can 936 and 938 can be individual actuator structures. The actuators 936 and 938 provide multiple degrees of freedom for each of the plurality of cameras 932 and 934. This way, the cameras 932 and 934 can be pointed at any desired location on the device being inspected.

The actuators can be controlled by a computing device 940 through an interface 942. The computing device can be any type of computing device, including a personal computer, a laptop or even a specially designed computer. The position and orientation of the actuators 936 and 938 relative to the device being inspected are controlled by a user interface that is part of the computing device 920. User interfaces that can be used include a mouse, a keyboard, a keypad, a touch screen and a joystick. These are provided as part of the computing device.

The system includes one or more displays 944 connected to each of the plurality of cameras 932 and 934. In one embodiment of the present invention, each of the cameras 932 and 934 are connected to a display 944. In accordance with another aspect of the present invention, one camera can be individually connected to one display.

One or more CAD models of a plurality of devices that can be inspected are stored in a memory 948. The memory 948 can be part of a remote server that is accessed by the computing device 940 in a remote manner. The memory 948 includes a CAD model of the device 930 being inspected.

The computing device 940 renders a virtual image of the device being inspected from the CAD model of the device being inspected. This can be performed using publicly available software, such as openGL. The computing device 940 can render a complete virtual image of the entire device being inspected or can render a virtual image of sections of the device being inspected to save time.

The position and orientation of the cameras 932 and 934 are controlled from a user interface on the computing device 940 to obtain images of the device being inspected. In accordance with an aspect of the present invention, the images from the device being inspected and the rendered virtual image are displayed simultaneously.

Figure 10:
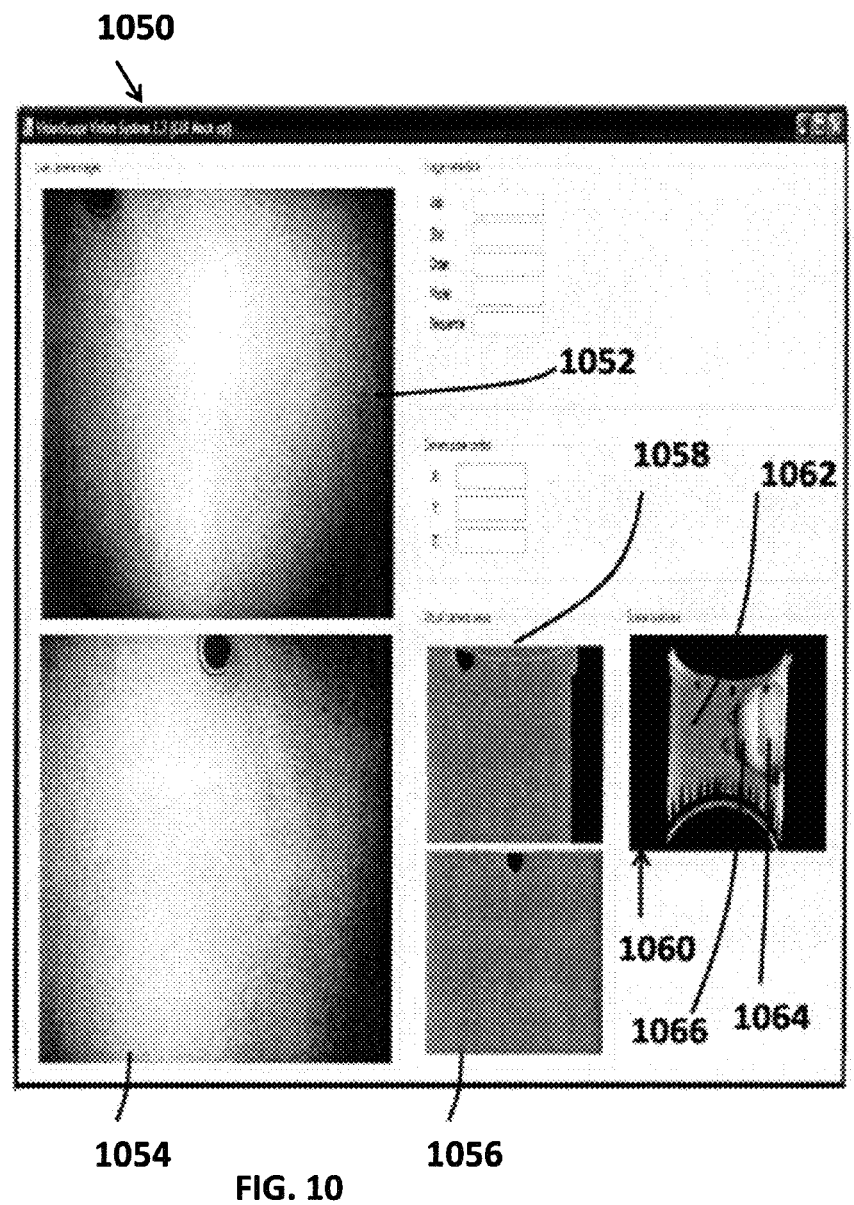
FIG. 10 illustrates an image generated in accordance with an aspect of the present invention.

FIG. 10 illustrates a window 1050 displayed by the computing device 1040. Images 1050 and 1052 are live images from the device being inspected. If there are defects, such as scars, cracks, decoloration, etc., those defects would appear here. However, simply examining these images may leave the inspector uncertain about their positions in the device being inspected. The inspector may also be uncertain about the nature of the device being inspected and whether there is in fact a defect.

Thus, the present invention also displays rendered virtual images related to the live images as images 1058 and 1056. Thus, live image 1052 is related to rendered virtual image 1058. Also, live image 1054 is related to rendered virtual image 1056.

In general, the virtual images are rendered from the CAD model with given virtual camera positions and internal characteristics. To establish the correlation between the virtual image and live image, the virtual camera must have the same position and internal characteristics as the live camera. An internal calibration process estimates the internal characteristics of the live camera. After an external calibration process, the position of the live camera regarding to the CAD model at any time is calculated from the actuator positional readings.

Once the positional and internal parameters of the live cameras are obtained, they are used by the virtual cameras to render from CAD model the virtual image 1056 or 1058 using computer graphics technologies such as OpenGL. The virtual image and live image show similar structures, such as the hole at the top center of live image 1054 and virtual image 1056.

Thus, aspects of the present invention allow a live image of a device being inspected to be displayed with a rendered virtual image. In accordance with an aspect of the invention, the live image 1054 is displayed adjacent the rendered virtual image 1056. The images can be displayed side by side. This allows defects in the device under inspection to be more readily identified because the inspector can view a model of the device in its unused state while examining an image of the device being inspected that has been used.

Additionally or alternatively, the live video image 1052 can be overlaid as image 1064 on a larger version of the rendered virtual image 1062 in a window 1060. This is done by correlating the position.

The computing device knows the position and orientation of the cameras because the actuator reports its position to the computing device. Also, the needed physical characteristics of the cameras can be transmitted through the actuator interface to the computing device. Alternatively, the physical characteristics of the cameras can be stored in memory and accessed by the computing device as needed. The computing device uses this information to locate the live images 1064 and 1066 on the rendered virtual image 1062.

As shown in FIG. 10, multiple images 1064 and 1066 can be overlaid on the rendered virtual image 1062 of the device under inspection.

The display 1060 helps the inspector to readily identify the location of the image and of any defect located in the live images 1052 and 1054.

The inspection station of the present invention can be used in different modes. In a first mode, live images, generating from a real time inspection of the device being inspected are fed to the computing device. In this case, the computing device performs the steps described above in real time and can be used to control the location of the actuators and therefore the cameras.

In accordance with another aspect of the present invention, the images of the device can be generated using the cameras and movable controllable actuators and those images stored in a memory. When time for analysis comes, the images are stored in a memory accessible by the computing device.

The computing device, as before, has access to a CAD model of the device being inspected. The computing device renders a virtual image of the device being inspected from the CAD model using, for example, openGL. The computing device then causes one or more of the live images to be displayed simultaneously with the rendered virtual image.

The display of the live images and the rendered virtual image are either side-by-side or in an overlay manner as described above or both. The side by side display and the overlay display are shown in FIG. 10.

The device being inspected is arranged in a known location to the cameras/actuators prior to the inspection. This allows the computing device to relate the images to an appropriate section of the CAD model of the device. This is referred to as calibration. The calibration can be performed manually and the details of the calibration reported to the computing device.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the scope of the claims.

The invention claimed is:

1. A method for inspecting a turbine with an inspection computer and a camera, comprising: with a wireless mobile device, establishing wireless connectivity with the inspection computer;
    selecting a stream of interest of images of the turbine and a region of interest within the stream of interest with the wireless mobile device;
    the wireless mobile device requesting the stream of interest and the region of interest from the inspection computer and then receiving images representing the region of interest in the stream of interest from the inspection computer;
    the wireless mobile device displaying the region of interest;
    sending a request to the inspection computer for a model of the turbine in the region of interest and for an image of the turbine in the region of interest;
    receiving the model of the turbine and the image of the turbine in the region of interest from the inspection computer; and
    displaying the model of the turbine and the image of the turbine in the region of interest on the wireless mobile device.

2. The method of claim 1, wherein a list of a plurality of streams of interest is displayed on the mobile wireless device and the stream of interest is selected from the list and the region of interest received from the inspection computer is retrieved from a memory connected to the inspection computer.

3. The method of claim 1, wherein a list of a plurality of streams of interest is displayed on the mobile wireless device and the stream of interest is selected from the list and the region of interest received from the inspection computer is retrieved from the camera connected to the inspection computer.

4. The method of claim 1, wherein the wireless mobile device selects a frame per second parameter for the image stream of interest and the inspection computer sends the image stream of interest to the wireless mobile device in accordance with the selected frame per second.

5. The method of claim 4, wherein the selected frame per second is less than 30 frames per second.

6. The method of claim 1, comprising the wireless mobile device sending probe control signals to the inspection computer and the inspection computer processing the probe control signals to send processed probe control signals to control a probe.

7. The method of claim 1, comprising the wireless mobile device sending camera control signals to the inspection computer and the inspection computer processing the camera control signals to send processed camera control signals to control the camera.

8. The method of claim 1, comprising the wireless mobile device sending trigger control signals to the inspection computer and the inspection computer processing the trigger control signals to send processed trigger control signals to control a trigger board.

9. The method of claim 1, comprising the wireless mobile device:
    sending probe control signals to the inspection computer and the inspection computer processing the probe control signals to send processed probe control signals to control a probe;
    sending camera control signals to the inspection computer and the inspection computer processing the camera control signals to send processed camera control signals to control the camera; and
    sending trigger control signals to the inspection computer and the inspection computer processing the trigger control signals to send processed trigger control signals to control a trigger board.

10. The method of claim 1, further comprising:
    the inspection computer transmitting the region of interest within the stream of interest of images at a frame rate that depends on a transmission quality with the wireless mobile device.

11. A system to inspect a turbine with an inspection computer and a camera, comprising:
    a wireless mobile device, enabled to establish wireless connectivity with the inspection computer, wherein the wireless mobile device includes a processor enabled to execute instructions to perform the steps:
    selecting a stream of interest of images of the turbine and a region of interest within the stream of interest;
    requesting the stream of interest and the region of interest from the inspection computer and then receiving images representing the region of interest in the stream of interest from the inspection computer;
    displaying the region of interest on a display;
    sending a request to the inspection computer for a model of the turbine in a region of interest and for an image of the turbine in the region of interest;
    receiving the model of the turbine and the image of the turbine in the region of interest from the inspection computer; and
    displaying the model of the turbine and the image of the turbine in the region of interest on the wireless mobile device.

12. The system of claim 11, wherein a list of a plurality of streams of interest is displayed on the mobile wireless device and the stream of interest is selected from the list and the region of interest received from the inspection computer is retrieved from a memory connected to the inspection computer.

13. The system of claim 11, wherein a list of a plurality of streams of interest is displayed on the mobile wireless device and the stream of interest is selected from the list and the region of interest received from the inspection computer is retrieved from the camera connected to the inspection computer.

14. The system of claim 11, wherein the wireless mobile device selects a frame per second parameter for the image stream of interest and the inspection computer sends the image stream of interest to the wireless mobile device in accordance with the selected frame per second.

15. The system of claim 14, wherein the selected frame per second is less than 30 frames per second.

16. The system of claim 11, comprising the wireless mobile device sending probe control signals to the inspection computer and the inspection computer processing the probe control signals to send processed probe control signals to control a probe.

17. The system of claim 11, comprising the wireless mobile device sending camera control signals to the inspection computer and the inspection computer processing the camera control signals to send processed camera control signals to control the camera.

18. The system of claim 11, comprising the wireless mobile device sending trigger control signals to the inspection computer and the inspection computer processing the trigger control signals to send processed trigger control signals to control a trigger board.

19. The system of claim 11, further comprising:
    the inspection computer transmitting the region of interest within the stream of interest of images at a frame rate that depends on a transmission quality with the wireless mobile device.

* * * * *